(12) United States Patent
Goudy et al.

(10) Patent No.: US 10,398,810 B2
(45) Date of Patent: Sep. 3, 2019

(54) NASAL SUCTION DEVICE

(71) Applicant: BeeClear, LLC, Decatur, GA (US)

(72) Inventors: Steven L. Goudy, Decatur, GA (US); Sudarsan Pranatharthikaran, Dayton, NJ (US); Siddhant Kumar Chawla, Dublin, OH (US); Ankit Raghuram, Morganville, NJ (US); Catherine Gu, Suwanee, GA (US); Young Kyoung Kim, Yuseong-gu Daejeon (KR); Suhaas Anbazhakan, Delray Beach, FL (US)

(73) Assignee: BeeClear, LLC, Decatur, GA (US)

( * ) Notice: Subject to any disclaimer, the term of this patent is extended or adjusted under 35 U.S.C. 154(b) by 158 days.

(21) Appl. No.: 15/368,383

(22) Filed: Dec. 2, 2016

(65) Prior Publication Data

US 2017/0157305 A1  Jun. 8, 2017

Related U.S. Application Data

(60) Provisional application No. 62/495,580, filed on Dec. 2, 2015.

(51) Int. Cl.
*A61M 1/00* (2006.01)

(52) U.S. Cl.
CPC ........ *A61M 1/0039* (2013.01); *A61M 1/0001* (2013.01); *A61M 1/008* (2013.01);
(Continued)

(58) Field of Classification Search
CPC .............. A61M 1/0039; A61M 1/0001; A61M 1/0066; A61M 1/008; A61M 2205/10; A61M 2210/0618
See application file for complete search history.

(56) References Cited

U.S. PATENT DOCUMENTS 2,890,699 A  6/1959  Miller
5,722,575 A  3/1998  Smith
(Continued)

FOREIGN PATENT DOCUMENTS

EP  1474186  11/2004
EP  1474186   5/2006
(Continued)

OTHER PUBLICATIONS

Brungart, Timothy A., "Modifications of a handheld vacuum cleaner for noise control." The Journal of the Acoustical Society of America 49(2), 2001.
(Continued)

*Primary Examiner* — Amber R Stiles
(74) *Attorney, Agent, or Firm* — Brient IP Law, LLC

(57) ABSTRACT

In various embodiments, a nasal aspirator has a suction device having an input port, a nasal aspirator tip having a first body portion and a second body portion that is releasably coupled to the first body portion. The second body portion has an input port that is in fluid communication with an output port that is formed on the first body portion. A hollow tube has a first end that is coupled to the suction device input port and a second end that is coupled to the first body output port. In some embodiments, the suction device is configured to be releasably attached to the body of a user via a strap and the nasal aspirator tip is configured to be grasped between two adjacent fingers on the user's hand while leaving at least two other fingers on the user's hand free to manipulate the head of a child on which the nasal aspirator is being used.

20 Claims, 11 Drawing Sheets

(52) U.S. Cl.
CPC ....... *A61M 1/0066* (2013.01); *A61M 2205/10* (2013.01); *A61M 2210/0618* (2013.01)

(56) References Cited

U.S. PATENT DOCUMENTS

| | | | |
|---|---|---|---|
| 5,800,425 A * | 9/1998 | DeLeonardis | A61M 1/0023 600/573 |
| 6,290,667 B1 | 9/2001 | Cook | |
| 6,517,511 B2 | 2/2003 | Yao | |
| 7,167,573 B2 | 1/2007 | Williamson | |
| 7,862,536 B2 | 1/2011 | Chen et al. | |
| 7,959,597 B2 | 6/2011 | Baker et al. | |
| 8,696,648 B2 | 4/2014 | Laerdal et al. | |
| D712,535 S | 9/2014 | Du | |
| 9,144,635 B1 * | 9/2015 | Kaplan | A61M 1/0009 |
| 9,192,701 B2 | 11/2015 | Lambert | |
| 9,408,969 B2 | 8/2016 | Tanaka et al. | |
| 2003/0225427 A1 * | 12/2003 | Chen | A61M 1/0058 606/162 |
| 2005/0049620 A1 | 3/2005 | Chang | |
| 2007/0270736 A1 | 11/2007 | Giarrocco-Brettner | |
| 2009/0105674 A1 * | 4/2009 | Cheng | A61M 1/0001 604/320 |
| 2010/0241155 A1 | 9/2010 | Chang et al. | |
| 2013/0203013 A1 * | 8/2013 | Taddeo | A61C 17/04 433/94 |
| 2013/0245560 A1 | 9/2013 | Guillem Garcia et al. | |
| 2014/0296793 A1 * | 10/2014 | Varney | A61M 1/0003 604/212 |

FOREIGN PATENT DOCUMENTS

| | | |
|---|---|---|
| EP | 2005981 | 12/2008 |
| EP | 2754455 | 7/2014 |

OTHER PUBLICATIONS

NoseFrida. Fridababy website. http://fridababy.com/product/nosefrida/, Earliest availability date Oct. 21, 2015.

* cited by examiner

NASAL SUCTION DEVICE

CROSS-REFERENCE TO RELATED APPLICATIONS

This patent application claims priority to U.S. Provisional Patent Application No. 62/495,580, entitled "NasAid", filed Dec. 2, 2015, the entire disclosure of which is hereby incorporated by reference in its entirety.

BACKGROUND

Children typically experience upper respiratory infections (URI) often each year, where children in daycare may experience 10 or more URIs due to the close proximity of the children in a closed space. Treatment for a URI is mostly symptomatic focusing on fever reduction and removal of mucous from the nasal passageways. Nasal aspirators have been used particularly with young children to create a partial vacuum for suctioning nasal discharge from the child's nostril. A typical nasal aspirator includes an oval shaped bulb, a tip, and a stem. The bulb is generally made out of a rubber type of material that has an opening into an inner hollow cavity. The nasal aspirator is used by compressing the bulb which forces air out of the inner hollow cavity through an opening in the tip. The tip is then placed and aligned with the nasal passage of the child so as to create a seal between the tip and the nasal passage. Once in place, the compressed bulb is then released creating a temporary vacuum due to the pressure within the inner hollow cavity of the bulb being less than the pressure of the external environment. The pressure differential creates a partial vacuum causing suction at the opening of the tip. The nasal aspirator thus assists in cleaning and clearing the child's nasal passage. Prior art nasal aspirators require the user to grasp the bulb or body of the aspirator with the hand and fingers thus preventing the user from using their hand and fingers to maintain the child's head in the correct position.

Various embodiments of the present systems and methods recognize and address the foregoing considerations, and others, of prior art nasal aspirators.

SUMMARY

In various embodiments, a nasal aspirator comprises (1) a suction device having an input port; (2) a nasal aspirator tip having (a) a first body portion having a concave shaped right side wall and a concave shaped left side wall that are configured to allow a user to grip the first body portion using a first finger that is received (e.g. apposed) against the concaved shaped right side wall and a second finger that is received (e.g. apposed) against the concaved shaped left side wall; and (b) a second body portion releasably coupled to the first body portion, the second body portion having an input port that is in fluid communication with an output port that is formed on the first body portion; and (3) a hollow tubing having a first end that is coupled to the suction device input port and a second end that is coupled to the first body output port. In particular embodiments, the suction device input port is in fluid communication with the first body output port. In some embodiments, the suction device is configured to be releasably attached to the body of a user via a strap (e.g., on the user's forearm or upper arm).

In another embodiments, a nasal aspirator comprises (1) a motorized or mechanically actuated suction device having an input port, wherein the suction device is configured to be attached to a user by a strap that is coupled to the suction device; (2) a nasal aspirator tip body having (a) a first end, (b) a second end, (c) an output port proximate the first end, (d) an input port proximate the second end, and (e) a mucous reservoir removeably mounted within the nasal aspirator tip body intermediate the first end and the second end, the mucous reservoir defining a cavity that is in fluid communication with the input port and the output port of the nasal aspirator tip body, and (3) a hollow tubing having a first end that is coupled to the suction device input port and a second end that is coupled to the nasal aspirator tip body output port. In various embodiments, the suction device input port is in fluid communication with the nasal aspirator tip body input port. In some embodiments, the nasal aspirator tip body is located remote from the suction device. In various embodiments, the nasal aspirator tip input port is slanted relative to the centerline of the first body to create a larger effective area for suction or for more optimal positioning of the tip to the nostril.

In certain embodiments, the nasal aspirator tip body has a first side wall that is concave in shape with respect to the upper and lower surface of the side wall, and a second side wall that is concave in shape with respect to the upper and lower surface of the side wall. In these embodiments, the concave first and second side walls allow a user to grasp the aspirator tip body using two adjacent fingers on one hand so that the remaining fingers on the one hand can be used to manipulate the head of a child on which the nasal aspirator is being used. In still other embodiments, the nasal aspirator further comprises a finger bracket that is coupled to the nasal aspirator tip body intermediate the first end and the second end. In these embodiments, the finger bracket is configured to allow a user to grasp the aspirator tip body using two adjacent fingers on one hand so that the remaining fingers on the one hand can be used to manipulate the head of a child on which the nasal aspirator is being used, yet support the device to rest on the fingers. In yet other embodiments, the nasal aspirator tip body may comprise both the first and second concave side walls and the finger bracket to allow the user to grasp the nasal aspirator tip body with two fingers on the same hand.

In another embodiment, a nasal aspirator comprises (1) a motorized, or non-motorized user activated mechanical, suction pump device having an input port that is configured to pull a vacuum therethrough; (2) a nasal aspirator tip body having (a) a first end, (b) a second end, (c) a first side wall extending between the first end and the second end, wherein a portion of the first side wall is concave, (d) a second side wall extending between the first end and the second end, wherein a portion of the second side wall is concave, (e) an output port positioned proximate the first end, (f) an input port positioned proximate the second end, and (g) a mucous reservoir removeably mounted within the nasal aspirator tip body intermediate the first end and the second end, the mucous reservoir defining a cavity that is in fluid communication with the input port and the output port of the nasal aspirator tip body, and (3) a hollow tubing having a first end that is coupled to the suction device input port and a second end that is coupled to the first body output port. In various embodiments, the suction device input port is in fluid communication with the nasal aspirator tip body input port so that a vacuum pulled at the suction device input port is also pulled at the aspirator tip body input port. In some embodiments, the suction device is located remote from the nasal aspirator tip body, and may contain a secondary back-up reservoir chamber operatively coupled to the suction device input port, that is configured to prevent mucus from entering the suction device pump assembly.

BRIEF DESCRIPTION OF THE DRAWINGS

Various embodiments of a system and method for creating and displaying a presentation are described below. In the course of this description, reference will be made to the accompanying drawings, which are not necessarily drawn to scale, and wherein.

DETAILED DESCRIPTION

Figure 1:
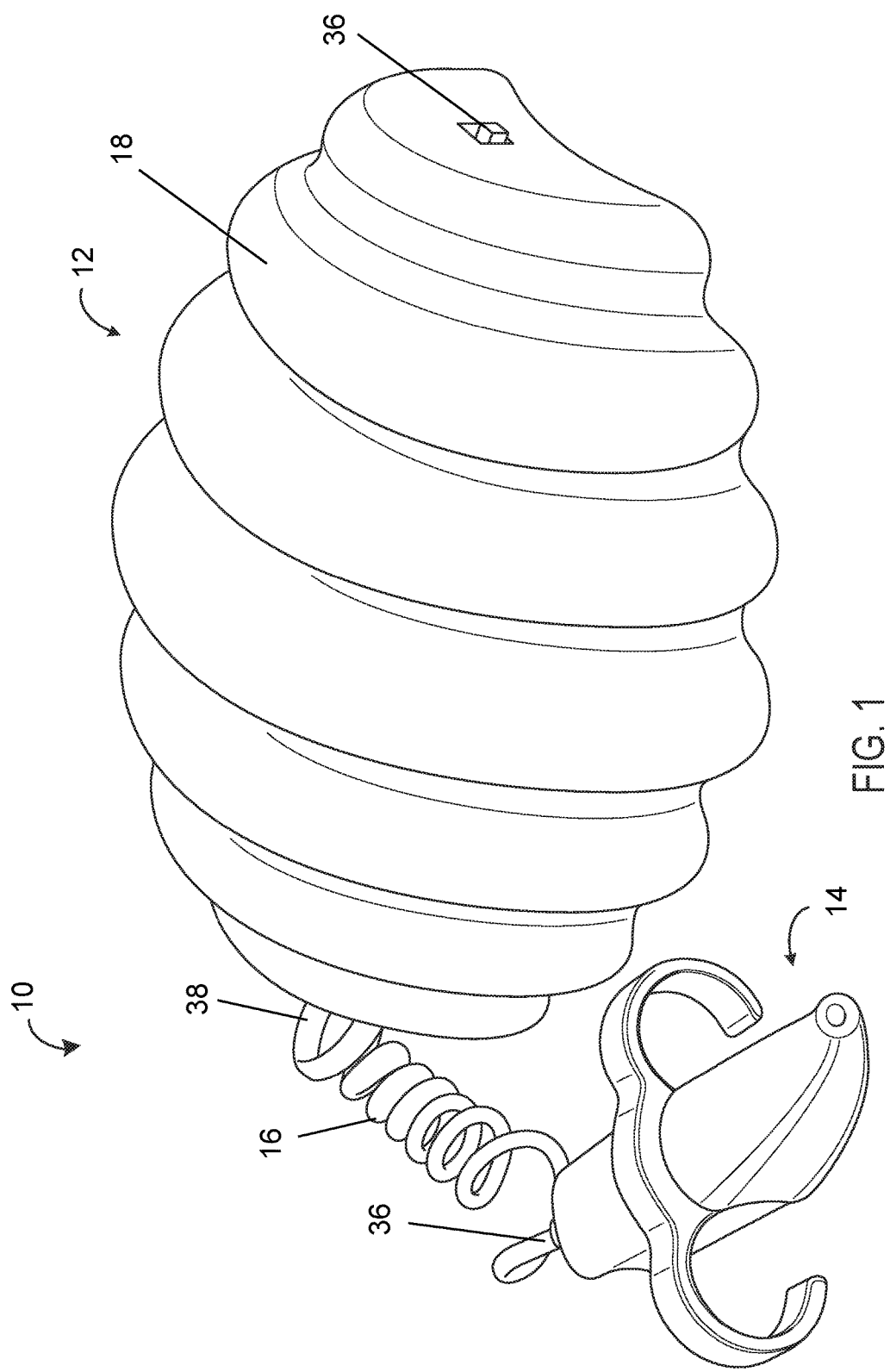
FIG. 1 is a perspective view of an embodiment of a nasal aspiration device.

Various embodiments will now be described more fully herein with reference to the accompanying drawings, in which various relevant embodiments are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A nasal aspirator device, according to various embodiments, is configured to enable a user to suction mucous from the nasal passage ways (e.g., the nostrils) of a child while allowing the user to utilize both hands to stabilize the child's head while operating the aspiration device. In various embodiments, the nasal aspiration device comprises a suction device that can be releasably mounted to the user's forearm or placed alongside the child, or on the floor. The suction device is operatively coupled to a nasal aspirator tip by a hollow tube such that suction created in the suction device causes a vacuum to be pulled through the nasal aspirator tip. Thus, the nasal aspirator tip is located remote from the suction device so that the noise of a motorized vacuum device (e.g., a motorized pump, fan, vacuum pump) is positioned away from the nasal aspirator tip. In various embodiments, a vacuum pulled through an input port of the suction device is pulled through the hollow tubing and through an input port on the nasal aspirator tip.

In various embodiments, the nasal aspirator tip comprises a body that has a first side wall and a second side wall that each contains a concave wall portion. The concave wall portions of the first side wall and the second side wall assist the user in maintaining their grasp of the nasal aspirator tip body by two fingers on the same hand so that the user can use the remaining fingers on that hand to control the movement of a child's head on which the nasal aspirator device is being used. Additionally, the nasal aspirator tip body may also comprise a finger bracket that is mounted on the nasal aspirator tip body intermediate a first end and a second end. The finger bracket assists in maintaining the user's fingers adjacent the concave portions in the first and second side wall so that the user could more easily maintain their grip on the nasal aspirator tip body.

In various embodiments, the nose piece may be designed to have a recessed cavity formed in a rear surface of the nasal aspirator tip such that a user can mount the nasal tip aspirator on the tip of their finger. In this way, the nasal tip aspirator acts like an extension of the finger making it intuitive to use and easy to control by the user. In other embodiments, the nasal tip aspirator may have a single concave portion along one of the outer surfaces that allow the user to place their finger adjacent to the concave surface. In some of these embodiments, a strap may secure the nasal aspirator tip to the user's finger. In these embodiments, the use of a single finger to secure the nasal aspirator tip provides freedom to use four fingers for positioning and handling of the infant's head.

Nasal Aspirator Device Structure

Suction Device

Figure 10:
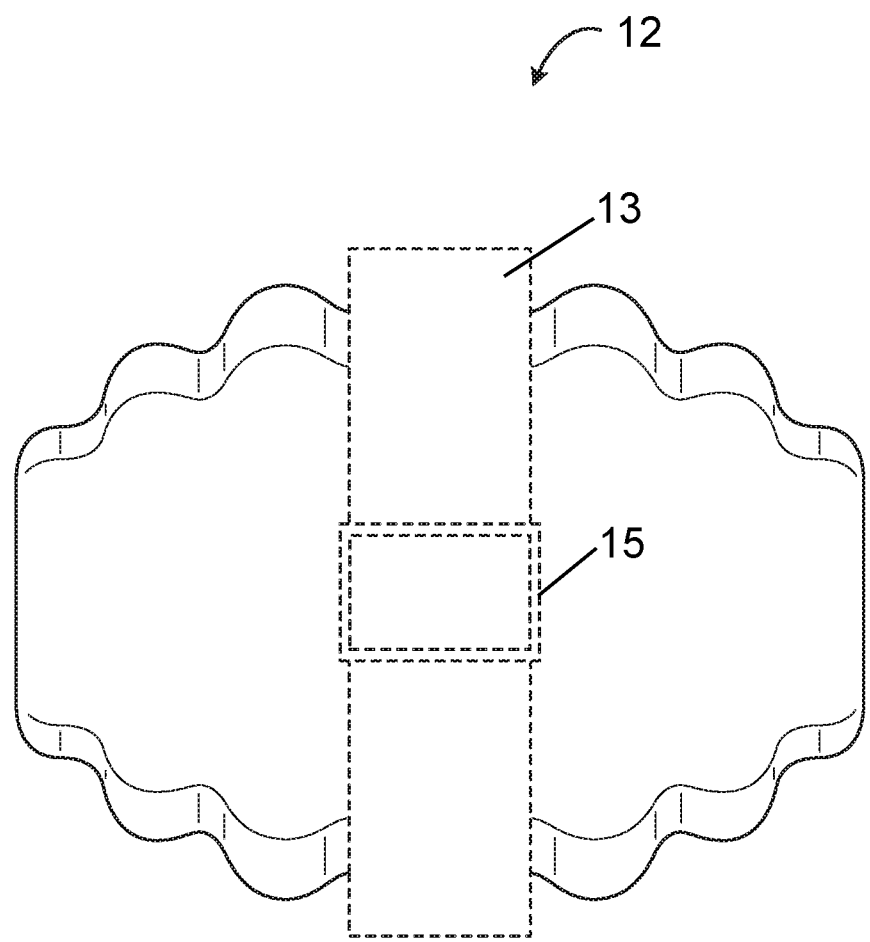
FIG. 10 is a bottom view of the suction device for use with the nasal aspiration device of FIG. 1.
Figure 11:
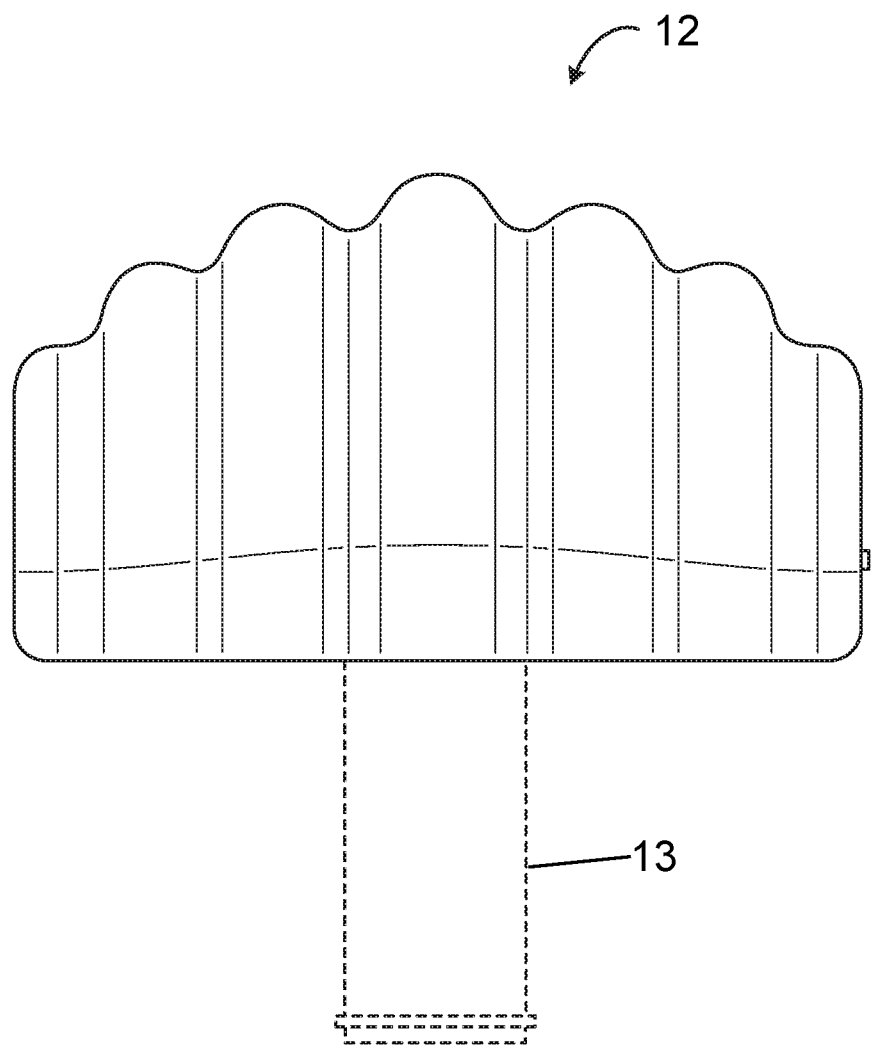
FIG. 11 is a right side view of the suction device for use with the nasal aspiration device of FIG. 1, the right left side view being similar to the right side view.
Figure 12:
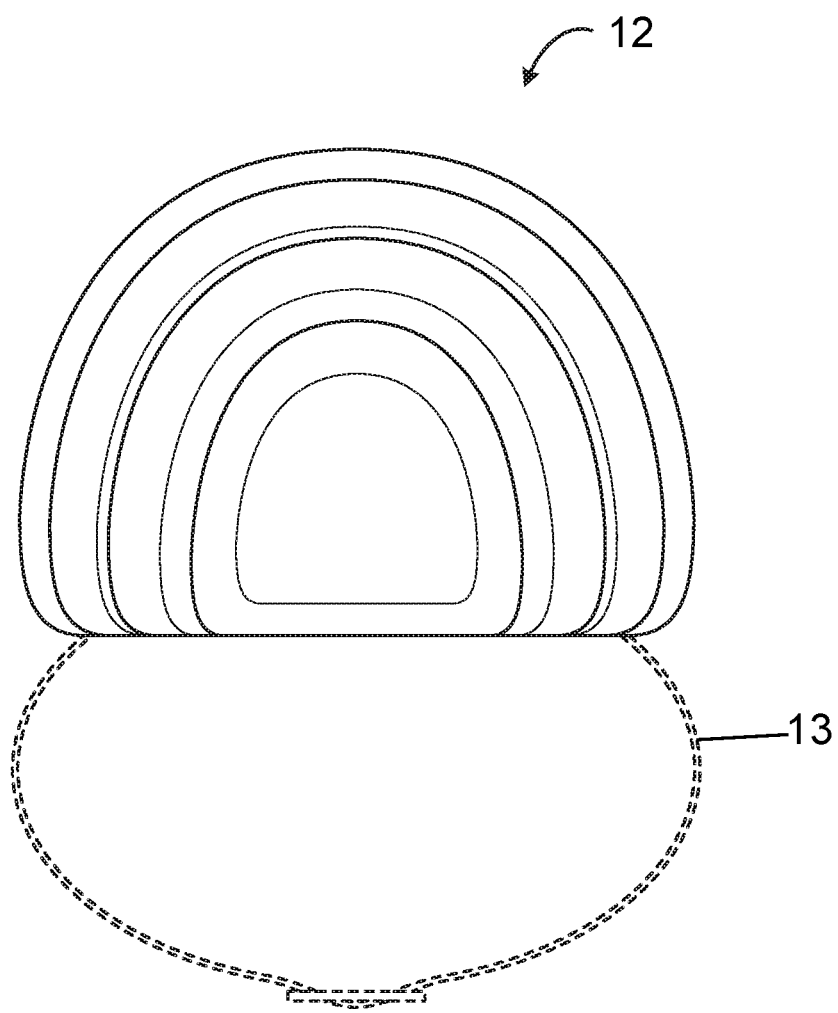
FIG. 12 is a front view of the suction device for use with the nasal aspiration device of FIG. 1, the back view being similar to the front view.

Referring to FIG. 1, a nasal aspirator 10 comprises a suction device 12, and a nasal aspirator tip 14. The nasal aspirator tip 14 is connected to the suction device 12 by a tube 16, as described in more detail herein. The suction device 12 may be positioned remotely from the nasal aspirator tip 14. In various embodiments, the suction device 12 may be attached to a user's arm (e.g., the forearm, upper arm, etc.) using a securing mechanism 13 (FIGS. 10-12), for example, an elastic strap, a strap and buckle 15 (FIGS. 10-12), etc. In various embodiments, the strap may be optional and the suction device 12 may be placed on a table or on the user's lap, or perhaps on the floor, etc. Similarly, the suction device could be non-motorized and contain a piston like suction apparatus that could be mounted upon the arm and pumped or placed on the floor and actuated by the user's foot.

Figure 2:
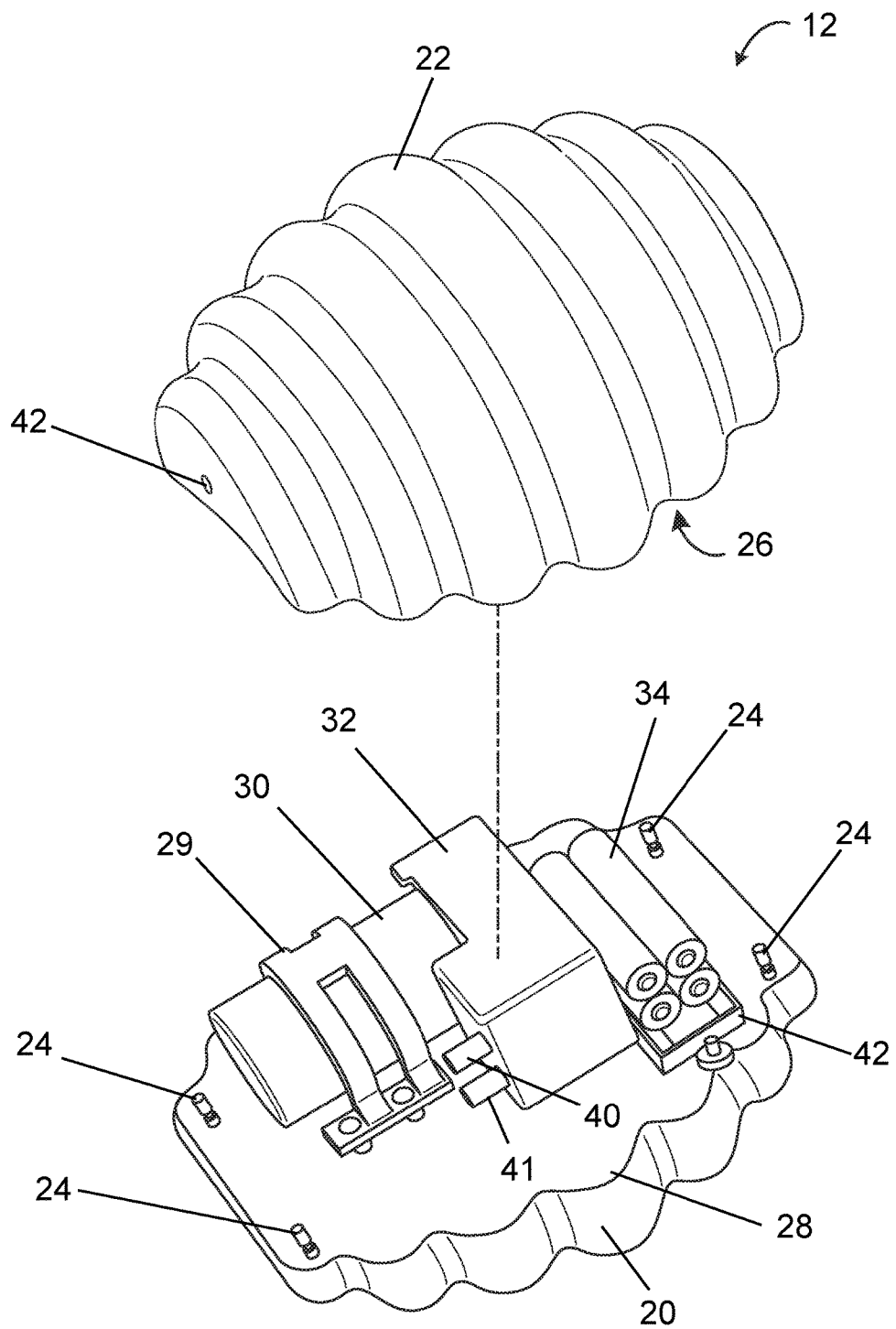
FIG. 2 is a partially exploded view of the nasal aspiration device of FIG. 1.
Figure 3:
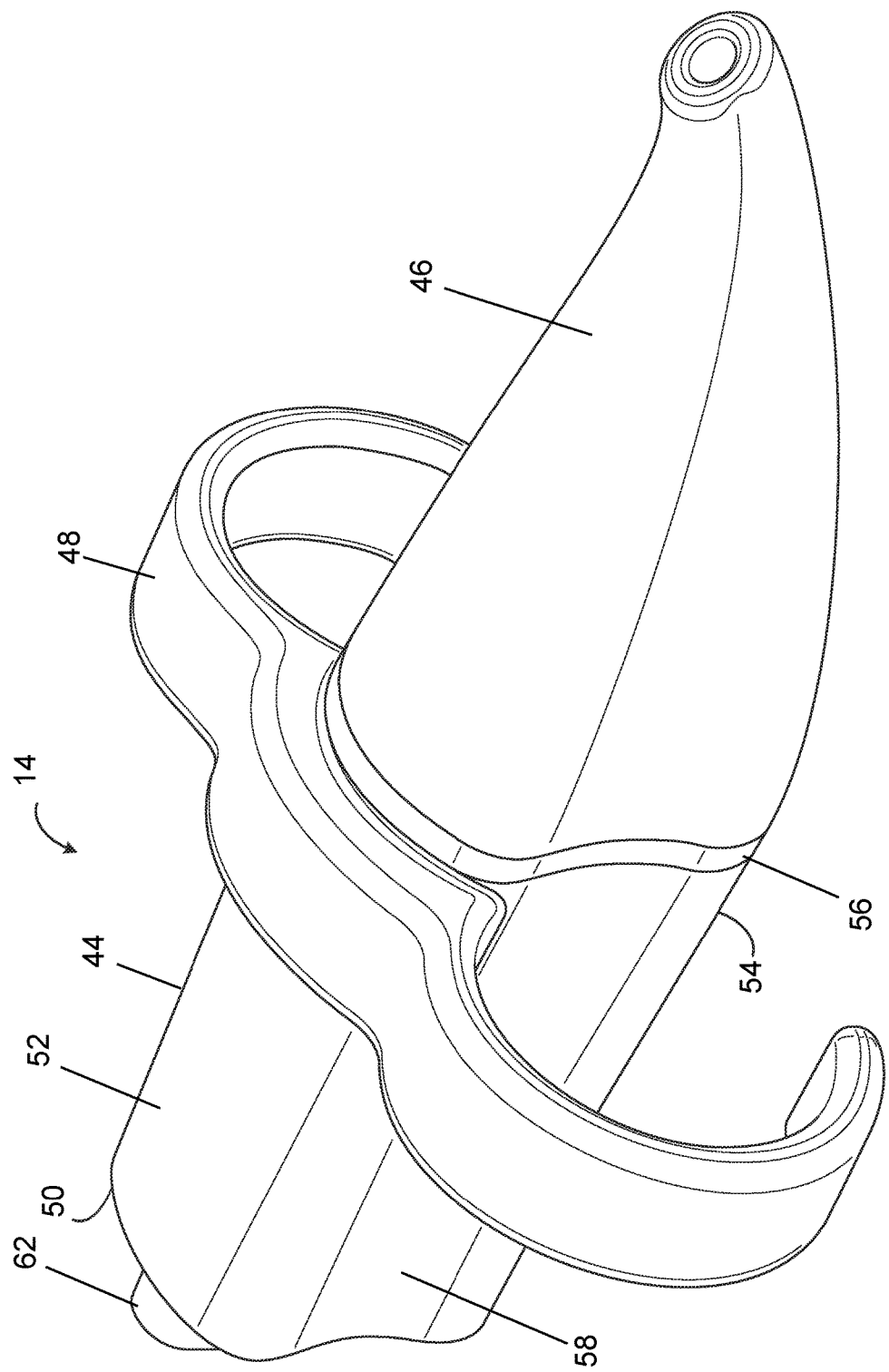
FIG. 3 is a perspective view of an embodiment of a nasal aspirator tip for use with the nasal aspiration device of FIG. 1.
Figure 4:
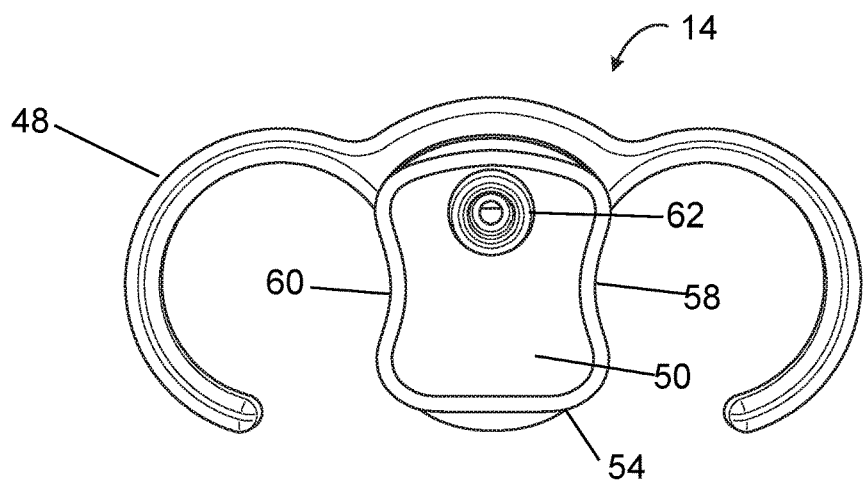
FIG. 4 is a rear view of the nasal aspirator tip of FIG. 3.
Figure 5:
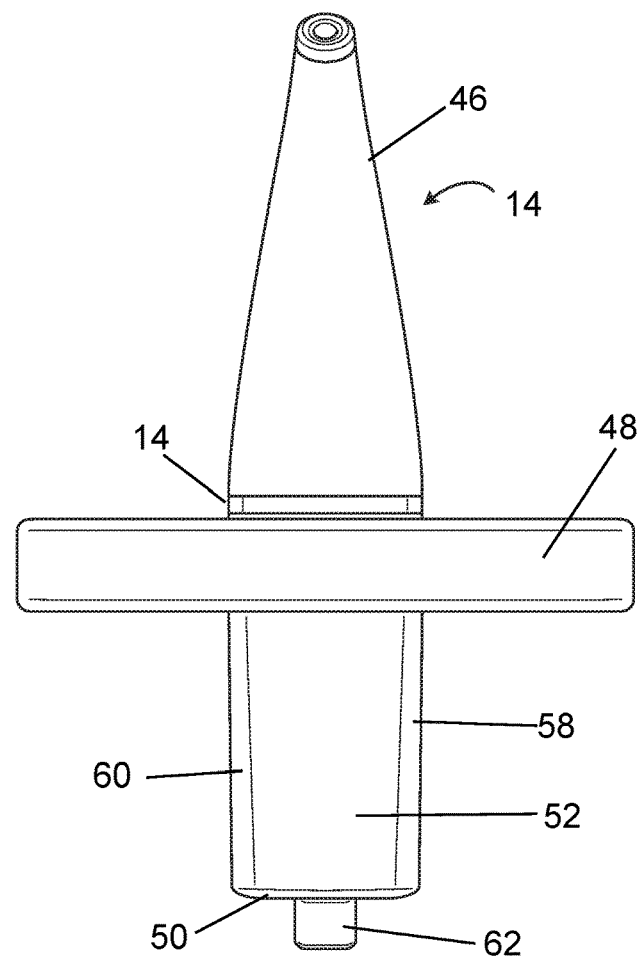
FIG. 5 is a top view of the nasal aspirator tip of FIG. 3.

Referring also to FIG. 2, the suction device 12 comprises a body 18 (FIG. 1) that is formed from a body bottom half 20 and a body top half 22 that together form a cavity 26 in which multiple parts of the suction device is housed. The body bottom and top halves 20 and 22 may be formed from any suitable material such as silicon, metal, aluminum, polymer, etc. or some combination thereof. In various embodiments, the body bottom and top halves 20 and 22 may be formed from a suitable polymer material such as polyethylene, polyethylene terephthalate, Nylon, etc. In some embodiments, the polymer material may be coated partially or completely with a silicon material. In particular embodiments, the body bottom and top halves 20 and 22 may be formed from an injection molding process.

The body top half 22 is releasably coupled to the body bottom half 20 by one or more fasteners 24. In various embodiments, the fasteners 24 may be screws, pins, rivets, etc. In various embodiments, multiple components are mounted to a top surface 28 of the body bottom half 20. The components include a vacuum creating device 30 (e.g., a motorized fan, a solenoid, a pump, etc.), a vacuum chamber 32, and a power source 34. The vacuum chamber 32 could be enlarged and separated to serve as a primary or secondary mucous collection chamber. In some embodiments this chamber could be removable for cleaning and serve as a backup chamber to the one contained within the nosepiece or alternatively serve as the only reservoir. The vacuum creating device 30, in particular embodiments, is an electrical pump (e.g., a piston pump, a blower, a turbine, a diaphragm pump, a roller pump, or combinations thereof) that draws a vacuum at an input port 40 of the vacuum chamber 32 and expels air out an output port 41 that is also coupled to the vacuum chamber 32. The vacuum creating device 30 is mounted to the top surface 28 of the body bottom half 20 by a bracket 29. It should be understood that the electric pump operates by creating a pressure differential between the input port 40 and the output port 41 such that the pressure at the output port 41 is higher than the pressure at the input port 40. The vacuum creating device 30 and vacuum chamber 32 together causes a vacuum to be pulled through the input port and expel air through the output port 41.

The power source 34 can be stored completely or partially in the cavity 26, for example in a battery compartment 42 that is formed through the body bottom half 20. The power source 34 may comprise, for example, one or more electric cells (e.g., batteries) that produce about 6 volts and approximately 2,500 mAh or be wall powered thru a transformer. The power source 34 may be rechargeable and can connect to an external electricity source (e.g., a 120V electrical wall outlet) to power the device and/or recharge the batteries. Additionally, the vacuum creating device 30 may have a power switch 36 (FIG. 1) that allows the user to power on/off the suction device 12.

In various embodiments and referring to FIGS. 1 and 2, the tube 16 has a first end 36 that is operatively coupled to the nasal aspirator tip 14 and a second end 38 that is operatively coupled to the vacuum chamber 32 at the input port 40. The second end 38 of the tube 16 passes through a hole 42 formed through the body top half 22. Thus, when a vacuum is pulled through the input port 40, the vacuum is also pulled through the nasal aspirator tip since the input port is in fluid communication with the nasal aspirator tip via the tube 16, as described in more detail below.

In various embodiments, an optional mucous reservoir can be operatively coupled to the input port 40 of the vacuum chamber. In these embodiments, the tube first end 36 would be operatively coupled to an input port of the optional mucous reservoir. Thus, should mucous be sucked up the tube 16, the optional mucous reservoir would prevent the mucous from being pulled into the vacuum assembly 30 and 32.

Nasal Aspirator Tip 14

Referring to FIGS. 3-7, the nasal aspirator tip 14 comprises a first body portion 44, a second body portion 46, and a finger bracket 48 that is coupled to one of the first body portion 44 or the second body portions 46. The first body portion 44 has a first end 50, a top surface 52, a bottom surface 54, a second end 56, and two side surfaces 58 and 60. An output port 62 is formed through the first end 50 and is operatively coupled to the first end 36 of tubing 16, as shown in FIG. 1. The first body portion has a cavity 64 defined therein that opens to the output port 62 and that also opens at the second end 54 of the first body portion 44. The cavity 64 is elongated with a generally rectangular cross-section that is similar to the cross section of the first body portion 44. An attachment flange 66 is formed at the first body portion second end 56 and is configured to releasably attach the first body portion second end 56 to the second body portion first end 68, for example, via a press fit connection or any other suitable gasket mechanism to provide a sealed connection to maintain a vacuum. In various embodiments, the first body portion 44 may be formed from a polymer via any suitable method such as injection molding, etc. The first body portion 44 may also be formed from a silicon material to make it compliant and flexible so that the user can easily grip the first body portion using a first finger and a second finger, as described herein. Additionally, the nasal aspirator tip 46 may be made of a softer silicone like material to enable softer, gentler apposition of the piece within the nostril while at the same time being rigid enough to maintain an adequate lumen for reliable vacuum flow. Similarly, the first body portion 44 could be composed of two materials, one softer on the outside, and another firmer material within the interior chamber to maintain an open lumen.

Figure 6:
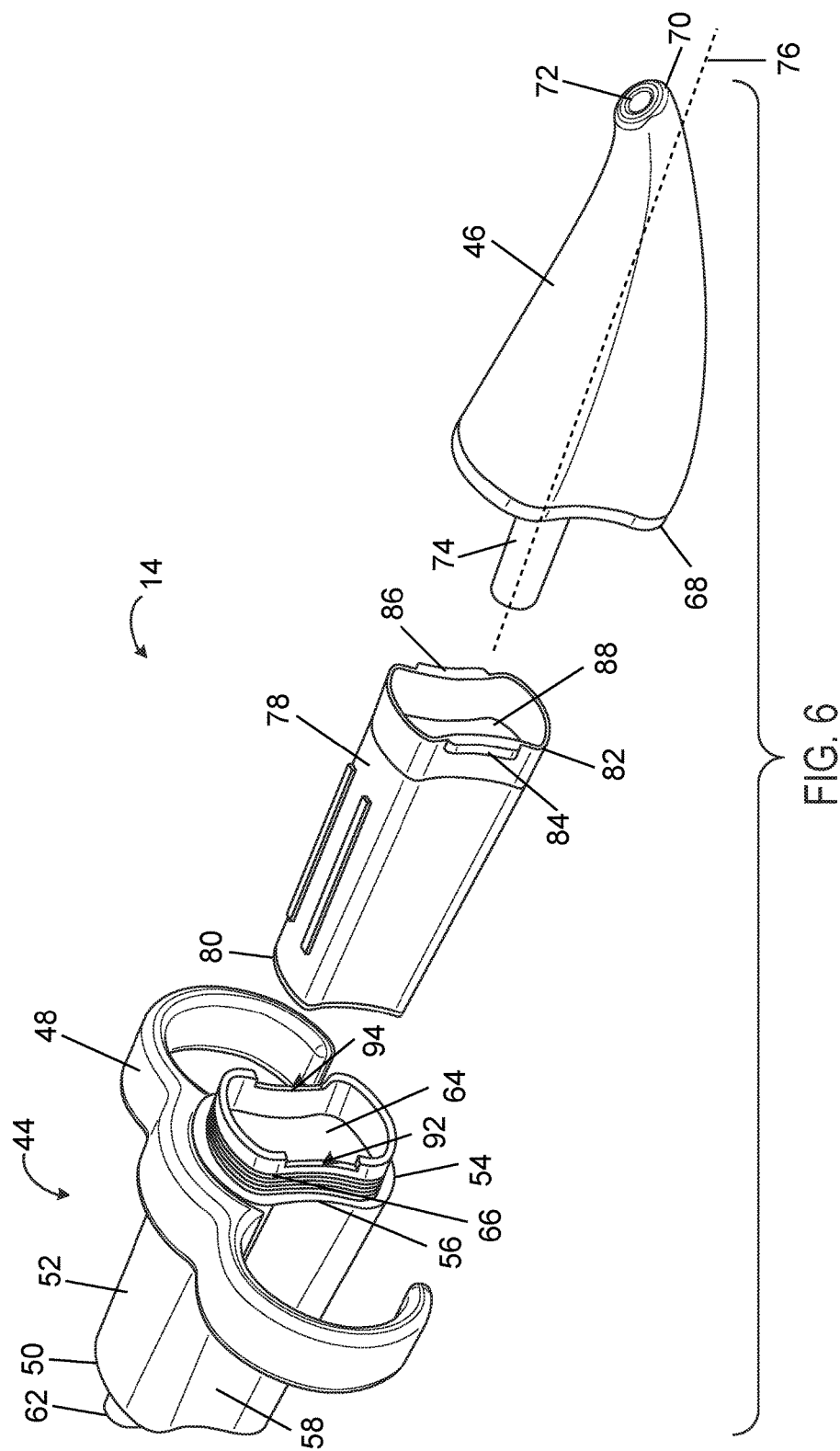
FIG. 6 is a right front perspective view of the suction tip of FIG. 3.
Figure 7:
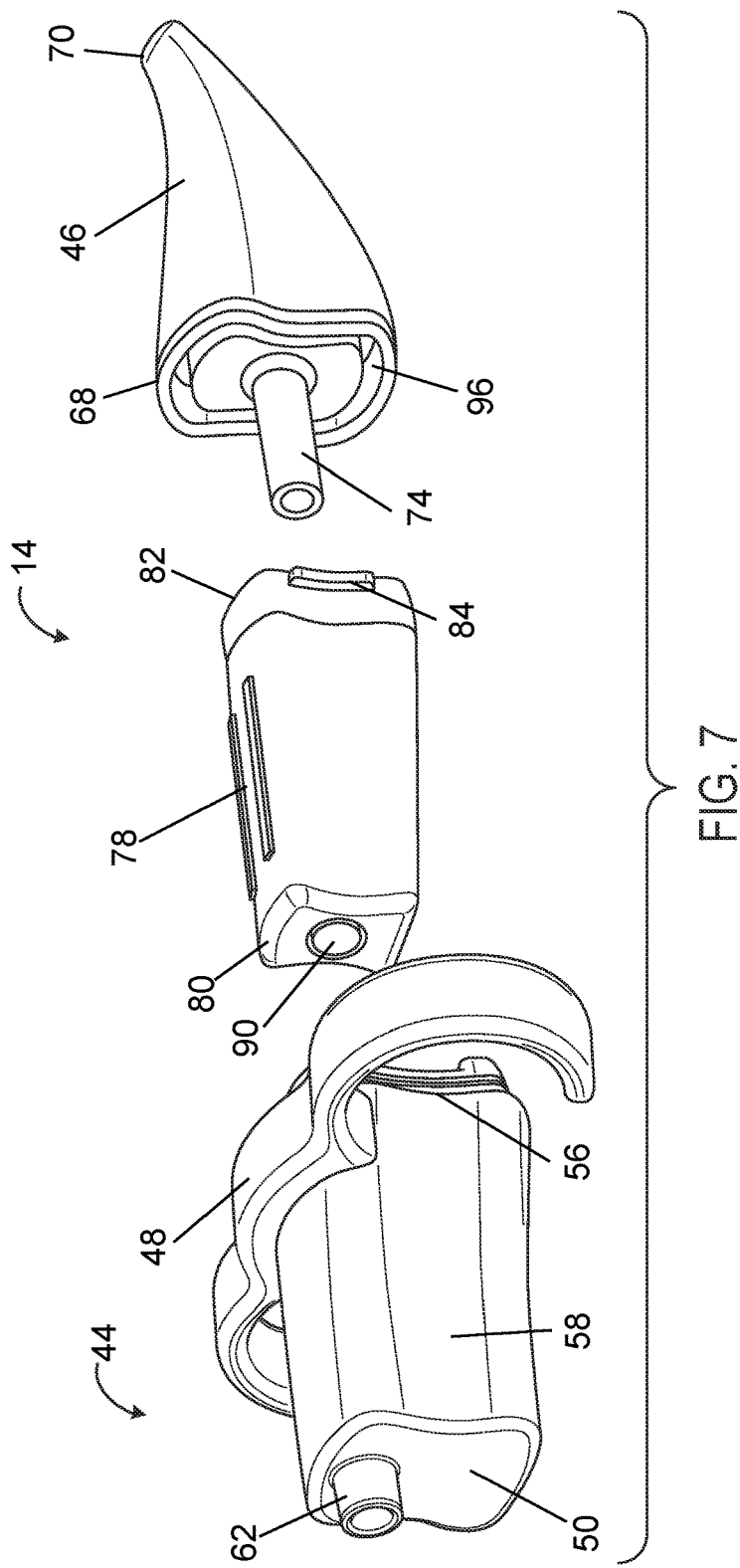
FIG. 7 is a right rear perspective view of the suction tip of FIG. 3.

Referring specifically to FIGS. 6-7, the second body portion 46 has the first end 68 and a second end 70. An input port 72 is formed at the second end 70, and an output port 74 is formed at the first end 68 of the second body portion 46. The input port 72 is in fluid communication with the output port 74 of the second body portion 46. The second end 70 of the second body portion 46 is offset from an axis 76 so that the second body portion second end 70 turns upward with respect to the axis 76. Said another way, a surface of the first end 50 of the first body portion 44 is angled with respect to a surface of the second end 70 of the second body portion 46. In this way, the offset second end makes it easier for the user to engage a child's nasal passages while gripping the nasal aspirator tip 14. It should also be understood that in other embodiments, the surface of the first end 50 of the first body 44 may be substantially parallel (e.g., parallel) with the surface of the second end 70 of the second body portion 46 depending on the use of the device.

Furthermore, because the input port 72 is at an angle relative to a centerline axis 76 of the first body portion cavity 64, the input port provides for a greater effective ease of apposition of the input port 72 to more ergonomically access the nostril so as to enter the nasal passage (e.g. the nostril) without injury. Additionally, the diameter of the input port increases from the second body portion second end 70 toward the first end 68 of the second body portion 46 thereby preventing the input port 72 from being placed too deep into the nasal passage of the child while the nasal aspirator tip 14 is in use. Finally, the second body portion 46 may be formed from silicon or from a polymer coated with silicon so as to provide a softer surface that minimizes the likelihood of causing injury when in use.

Still referring to FIGS. 6 and 7, a mucous reservoir 78 is sized and shaped to fit into the cavity 64 formed in the first body portion 44. The mucous reservoir 78 has a first end 80, a second end 82, first and second alignment flanges 84 and 86, and a cavity 88 that opens into an output port 90 (FIG. 7) and also to the mucous reservoir second end 82. In various embodiments, the output port 90 is formed toward the top of the first end 80 to help trap mucous within the collection chamber and prevent its migration into the suction device 32. In other embodiments, the output port 78 can be formed on a top surface of the mucous reservoir 78 to further prevent mucous from being sucked out of the mucous reservoir 78 through the output port 62 of the first body portion.

The mucus reservoir 78 is generally sized and shaped to be releasably received in the first body portion cavity 64 (FIG. 6) such that the alignment flanges 84 and 86 are received in two respective recessed portions 92 and 94 formed in the attachment flange 66 of the first body portion 44. Thus, when the nasal aspirator tip is assembled, the mucous reservoir 78 is inserted into the first body portion cavity 64 until the alignment flanges 84 and 86 are seated in the respective recessed portion 92 and 94. Once in this position, the second body portion is releasably coupled to the first body portion via the attachment flange 66, which is received in a groove 96 formed in the second body portion first end 68. Once assembled, the second body portion input port 72 is in fluid communication with the first body portion output port 62 such that a vacuum pulled at the output port 62 causes a vacuum to be pulled at the input port 72. To assure that no mucous finds its way back into the vacuum assembly (i.e., the pump 30 and vacuum chamber 32), in various embodiments a optional mucous reservoir that is readily removable may be positioned intermediate the vacuum chamber input port 40 and the tube first end 38 to catch any mucous that might escape the confines of the nasal aspirator tip's mucous reservoir chamber 78.

The mucous reservoir 78 helps to ensure that the mucous is collected without being sucked out of the first body portion output port 62 into the vacuum pumping assembly, suction device 12. Referring specifically to FIG. 7, it can be seen that when the second body portion 46 is attached to the first body portion 44, the output port 74 of the second body portion only extends partially within the mucous reservoir cavity 88 (FIG. 6), preferably to the upper portion of this chamber, so that any mucous that is sucked into the input port 70 of the second body portion 46 drops into the mucous reservoir 78 without getting sucked through the mucous reservoir output port 90.

Additionally, the mucous reservoir output port 90 is offset from the first body portion output port 62 so that mucous in the mucous reservoir 78 is not sucked out from the first body output port 62. This configuration helps to ensure that mucous is not accidently sucked into the suction tube 16 (FIG. 1) and back into the suction device 12. In particular embodiments, the mucous output port 90 may also be located on a top surface of the mucous reservoir 78 instead of on the first end 80 to further prevent mucous from being sucked through the first body portion output port 62. That is, because there is the possibility that the user might position the nasal aspirator tip 14 in such a way as to have mucous sucked out into the tube first end 36, optimally a second mucous reservoir (not shown) may be provided, of similar design as mucous reservoir 78, within the pump assembly, as a backup chamber, to avoid mucous finding its way into the vacuum assembly and causing maintenance or reliability issues.

Exemplary Nasal Aspirator Device Operation

Figure 8:
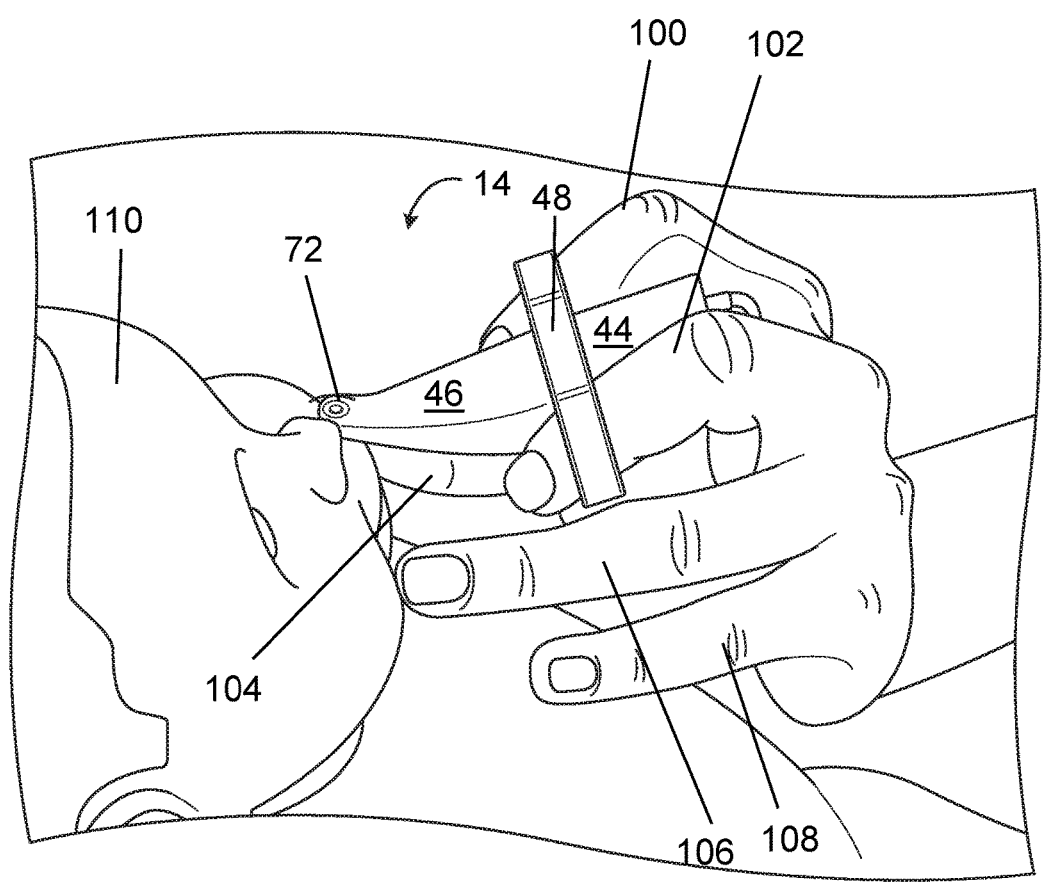
FIG. 8 is a perspective view of the suction tip of FIG. 3 in use on a child.
Figure 9:
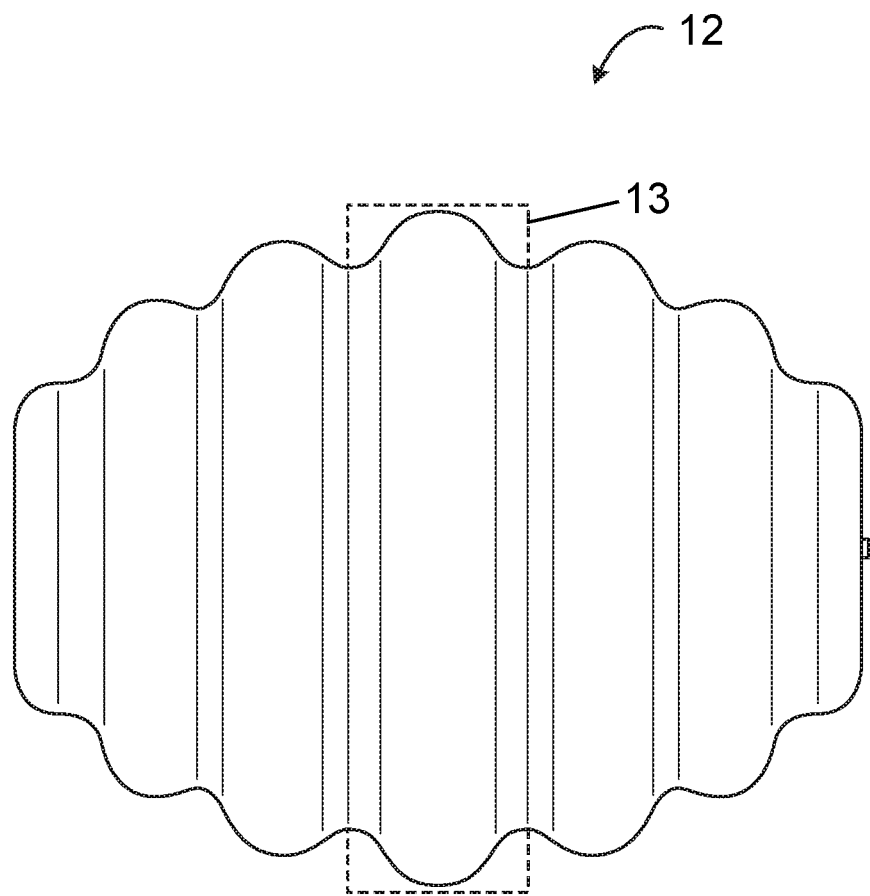
FIG. 9 is a top view of the suction device for use with the nasal aspiration device of FIG. 1.

Referring to FIG. 8, the nasal aspirator device 10 is shown in use by a caregiver and child. The user may secure the suction device 12 to their forearm, place it on a table (e.g., a changing table) or place it anywhere that is remote from the nasal aspirator tip 14. In the figure, the user is shown grasping the first body portion first and second concave walls 58 and 60 (FIG. 4) using their pointer finger 100 and middle finger 102. In the embodiment shown in the figure, the user's pointer finger 100 and middle finger 102 are also received in the finger bracket 48 to help secure the body first portion 44. However, it should be understood that in other embodiments, the finger bracket 48 may not be included, or other finger arrangements can be used to secure the nasal aspirator tip 14. In any case, the user is able to securely hold the nasal aspirator tip using two fingers on the same hand.

Continuing with this example, when using two finger (e.g. the pointer finger 100 and the middle finger 102) to grasp the nasal aspirator tip 14, the user has use of their thumb 104, ring finger 106 and pinky finger 108 to support, maintain and stabilize the child's head 110 in the proper position to engage the input port 72 in the child's nasal passage (e.g., nostril). Maintaining the child's head 110 in the proper position can be carried out by stabilizing the child's cheeks or chin using the thumb 104 and ring finger 106, important in the safe management and execution of the procedure. Moreover, because the suction device 12 is mounted remote from the nasal aspirator tip 14, noise generated by the suction device 12 generally will not scare the child causing unnecessary movement.

Once the user is done using the aspirator device, the user may remove the mucous reservoir 78 and wash it without also having to clean the first body portion 44. Moreover, because the second body portion 46 is also removeably attached to the first body portion 44 and the mucous reservoir 78, the user can also separately wash the second body portion 46 after use.

Conclusion

Many modifications and other embodiments of the invention will come to mind to one skilled in the art to which this invention pertains having the benefit of the teachings presented in the foregoing descriptions and the associated drawings. For example, as will be understood by one skilled in the relevant field in light of this disclosure, the invention may take form in a variety of different mechanical and operational configurations as confirmed by the various embodiments disclosed herein. Therefore, it is to be understood that the invention is not to be limited to the specific embodiments disclosed and that the modifications and other embodiments are intended to be included within the scope of the appended exemplary concepts. Although specific terms are employed herein, they are used in a generic and descriptive sense only and not for the purposes of limitation.

We claim:

1. A nasal aspirator comprising:
   a. a suction device having an input port, wherein the suction device is configured to pull a vacuum through the input port;
   b. a nasal aspirator tip having:
      i. a first body portion having a right side wall and a left side wall that are configured to allow a user to grip the first body portion using a first finger that is apposed against the right side wall and a second finger that is apposed against the left side wall, the right side wall and the left side wall defining a cavity therebetween;
      ii. a second body portion releasably coupled to the first body portion, the second body portion having
         a. an input port that is in fluid communication with an output port that is formed on the first body portion and that is configured to engage a nostril of a child on which the nasal aspirator is being used; and
         b. an output port;
   c. a finger bracket that is coupled to the nasal aspirator tip, wherein the finger bracket assists in allowing the user to further help to maintain position and grip on the nasal aspirator tip with their first and second fingers so that the remaining fingers on a hand of the user are free to support a child's head; and
   d. a hollow tubing having a first end that is coupled to the suction device input port and a second end that is coupled to the first body output port,
      wherein the suction device input port is in fluid communication with the first body output port, and
      wherein the first body portion and the second body portion are configured such that the flow of air or material from the output port of the second body portion through the cavity of the first body portion and through the output port of the first body portion is substantially parallel to a centerline axis extending through the nasal aspirator tip.

2. The nasal aspirator of claim 1, wherein the suction device is configured to be releasably attached to a body of the user.

3. The nasal aspirator of claim 2, wherein the first body portion right side wall further comprises a concave portion and the first body portion left side wall further comprises a concave portion that are configured to allow the user to grip the first body portion so that the first finger is apposed against the right side wall concave portion and the second finger is apposed against the left side wall concave portion.

4. The nasal aspirator of claim 1, wherein the second body portion input port is angled for entry access to a nostril.

5. The nasal aspirator of claim 1, wherein the second body portion of the nasal aspirator tip has:
  a. a first end that is configured to be releasably coupled to a second end of the first body portion; and
  b. a second end that defines the input port of the second body portion.

6. The nasal aspirator of claim 1, the nasal aspirator tip further comprising a mucous reservoir having an output port and an input port formed at a second end of the mucous reservoir, wherein
  a. the mucous reservoir is removeably positioned intermediate the first body portion and the second body portion, and
  b. the mucous reservoir is configured to receive aspirated mucous through the mucous reservoir input port and trap it to prevent the aspirated mucous from exiting the mucous reservoir output port.

7. The nasal aspirator of claim 6, wherein
the mucous reservoir is at least partially received in the cavity of the first body portion.

8. The nasal aspirator of claim 1, wherein the suction device is motorized.

9. A nasal aspirator comprising:
  a. a motorized suction device having an input port that is configured to pull a vacuum therethrough, wherein the suction device is configured to be attached to a user;
  b. a nasal aspirator tip body having:
    i. a first end,
    ii. a second end,
    iii. an output port proximate the first end,
    iv. an input port proximate the second end that is configured to engage a nostril of a child on which the nasal aspirator is being used,
    v. a mucous reservoir within the nasal aspirator tip body intermediate the first end and the second end, the mucous reservoir defining a cavity that is in fluid communication with the input port and the output port of the nasal aspirator tip body such that air and material flows substantially linearly through the mucous reservoir;
  c. a finger bracket that is coupled to the nasal aspirator tip body intermediate the first end and the second end, wherein the finger bracket is configured to allow the user to grasp the nasal aspirator tip body using two adjacent fingers on one hand so that the remaining fingers on the one hand can be used to manipulate a head of a child on which the nasal aspirator is being used; and
  d. a hollow tubing having a first end that is coupled to the suction device input port and a second end that is coupled to the nasal aspirator tip body output port, wherein
    the suction device input port is in fluid communication with the nasal aspirator tip body input port, and
    the nasal aspirator tip body is located remote from the suction device.

10. The nasal aspirator of claim 9, wherein the nasal aspirator tip body input port is angled for entry access to a nostril.

11. The nasal aspirator of claim 9, wherein the nasal aspirator tip body has a first side surface that is concave in shape and a second side surface that is concave in shape, wherein the concave first and second side surfaces allow the user to grasp the nasal aspirator tip body using two adjacent fingers on one hand so that the remaining fingers on the one hand can be used to manipulate a head of a child on which the nasal aspirator is being used.

12. The nasal aspirator of claim 9, wherein the nasal aspirator tip body proximate to the second end is curved with respect to the nasal aspirator tip body proximate to the first end so that the input port is aligned with a nostril opening of a child when the nasal aspirator tip body is being held by a child care provider.

13. The nasal aspirator of claim 9, wherein a body of the suction device is shaped such that a width of the body increases from each of two opposing ends toward a center portion having a maximum width, and wherein the body comprises a plurality of parallel circumferential rings or ridges extending from a first side of the body to an opposing second side of the body.

14. The nasal aspirator of claim 9, wherein the nasal aspirator tip body further comprises:
  a. a first body portion having:
    i. a first end,
    ii. a second end,
    iii. a cavity defined intermediate the first end and the second end, wherein the cavity opens to the second end,
      wherein the output port is formed proximate the first body portion first end and is in fluid communication with the cavity, and
  b. a second body portion having:
    i. a first end that is configured to be releasably attached to the first body portion second end,
    ii. a second end, wherein the input port is formed proximate the second body portion second end,
    wherein the mucous reservoir is defined by the first body portion cavity.

15. The nasal aspirator of claim 9, wherein the finger bracket comprises a first loop and a second loop, wherein the first loop is configured to receive a first finger on the user's hand and the second loop is configured to receive a second finger on the user's hand and to maintain the user's first finger adjacent a first side surface of the nasal aspirator tip body and the user's second finger adjacent a second side surface of the nasal aspirator tip body.

16. A nasal aspirator comprising:
  a. a suction device having an input port that is configured to pull a vacuum therethrough;
  b. a nasal aspirator tip body having:
    i. a first end,
    ii. a second end,
    iii. a first side wall extending between the first end and the second end, iv. a second side wall extending between the first end and the second end,
v. an output port positioned proximate the first end,
vi. an input port positioned proximate the second end, and
vii. at least a portion of the first side wall and of the second side wall that is configured to allow a user to secure the nasal aspirator tip body to at least one finger, wherein the at least a portion of the first side wall and of the second side wall defines a cavity therebetween that receives air and material flowing substantially linearly through the cavity, wherein the at least the portion of the first side wall and the second side wall comprises at least a concave portion that is part of a recessed cavity formed in the first end, and wherein the cavity is configured to allow a finger to be secured in the recessed cavity, and
c. a hollow tubing having a first end that is coupled to the suction device input port and a second end that is coupled to the nasal aspirator tip body output port, wherein
the suction device input port is in fluid communication with the nasal aspirator tip body input port so that a vacuum pulled at the suction device input port is also pulled at the nasal aspirator tip body input port, and
the suction device is located remote from the nasal aspirator tip body.

17. The nasal aspirator of claim 16, further comprising a strap that is coupled to the nasal aspirator tip body, wherein the strap helps to secure a finger in the at least a concave portion.

18. A nasal aspirator comprising:
a. a suction device having an input port, wherein the suction device is configured to pull a vacuum through the input port;
b. a nasal aspirator tip having:
    i. a first body portion having a right side wall and a left side wall that are configured to allow a user to grip the first body portion using a first finger that is apposed against the right side wall and a second finger that is apposed against the left side wall, the right side wall and the left side wall defining a cavity therebetween;
    ii. a second body portion releasably coupled to the first body portion, the second body portion having
        a. an input port that is in fluid communication with an output port that is formed on the first body portion and that is configured to engage a nostril of a child on which the nasal aspirator is being used; and
        b. an output port;
c. a mucous reservoir having an output port and an input port formed at a second end of the mucous reservoir, wherein i. the mucous reservoir is removeably positioned intermediate the first body portion and the second body portion, and
ii. the mucous reservoir is configured to receive aspirated mucous through the mucous reservoir input port and trap it to prevent the aspirated mucous from exiting the mucous reservoir output port; and
d. a hollow tubing having a first end that is coupled to the suction device input port and a second end that is coupled to the first body output port,
wherein the suction device input port is in fluid communication with the first body output port, and
wherein the first body portion and the second body portion are configured such that the flow of air or material from the output port of the second body portion through the cavity of the first body portion and through the output port of the first body portion is substantially parallel to a centerline axis extending through the nasal aspirator tip.

19. The nasal aspirator of claim 18, wherein the mucous reservoir is at least partially received in the cavity of the first body portion.

20. A nasal aspirator comprising:
a. a motorized suction device having an input port that is configured to pull a vacuum therethrough, wherein the suction device is configured to be attached to a user;
b. a nasal aspirator tip body having:
    i. a first end,
    ii. a second end,
    iii. an output port proximate the first end,
    iv. an input port proximate the second end that is configured to engage a nostril of a child on which the nasal aspirator is being used,
    v. a mucous reservoir within the nasal aspirator tip body intermediate the first end and the second end, the mucous reservoir defining a cavity that is in fluid communication with the input port and the output port of the nasal aspirator tip body such that air and material flows substantially linearly through the mucous reservoir, and
c. a hollow tubing having a first end that is coupled to the suction device input port and a second end that is coupled to the nasal aspirator tip body output port,
wherein
the suction device input port is in fluid communication with the nasal aspirator tip body input port,
the nasal aspirator tip body is located remote from the suction device, and
a body of the suction device is shaped such that a width of the body increases from each of two opposing ends toward a center portion having a maximum width, and wherein the body comprises a plurality of parallel circumferential rings or ridges extending from a first side of the body to an opposing second side of the body.

* * * * *